US009547782B2

(12) United States Patent
Lansdowne

(10) Patent No.: US 9,547,782 B2
(45) Date of Patent: Jan. 17, 2017

(54) IDENTIFICATION OF BIOLOGICAL SAMPLES

(71) Applicant: Research Instruments Limited, Cornwall (GB)

(72) Inventor: David C. Lansdowne, Falmouth (GB)

(73) Assignee: Research Instruments Limited, Cornwall (GB)

(*) Notice: Subject to any disclaimer, the term of this patent is extended or adjusted under 35 U.S.C. 154(b) by 0 days.

(21) Appl. No.: 14/950,665

(22) Filed: Nov. 24, 2015

(65) Prior Publication Data

US 2016/0078258 A1 Mar. 17, 2016

Related U.S. Application Data

(62) Division of application No. 11/597,532, filed as application No. PCT/GB2005/002048 on May 24, 2005, now Pat. No. 9,211,540.

(51) Int. Cl.
| | |
|---|---|
| *H04Q 5/22* | (2006.01) |
| *G06K 7/10* | (2006.01) |
| *B01L 3/00* | (2006.01) |
| *B01L 9/02* | (2006.01) |
| *G01N 35/00* | (2006.01) |

(52) U.S. Cl.
CPC ........... *G06K 7/10326* (2013.01); *B01L 3/545* (2013.01); *B01L 9/02* (2013.01); *B01L 2300/021* (2013.01); *B01L 2300/022* (2013.01); *B01L 2300/023* (2013.01); *G01N 2035/00782* (2013.01)

(58) Field of Classification Search
CPC combination set(s) only.
See application file for complete search history.

(56) References Cited

U.S. PATENT DOCUMENTS

| | | | |
|---|---|---|---|
| 5,036,308 | A | 7/1991 | Fockens |
| 5,912,622 | A | 6/1999 | Endo et al. |
| 6,184,846 | B1 | 2/2001 | Myers et al. |
| 6,677,852 | B1 | 1/2004 | Landt |
| 6,817,522 | B2 | 11/2004 | Brignone et al. |
| 6,827,279 | B2 | 12/2004 | Teraura |
| 6,838,278 | B2 | 1/2005 | Fortino |
| 7,016,325 | B2 | 3/2006 | Beasley et al. |

(Continued)

FOREIGN PATENT DOCUMENTS

| | | | | |
|---|---|---|---|---|
| EP | 1 467 620 | 5/2010 | ............... | A01N 1/02 |
| WO | WO 01/94016 | 12/2001 | ............... | B01J 19/00 |

OTHER PUBLICATIONS

Magus Nilsson, "Vitrolife acquires IVF Limited and starts direct sales of fertility media in UK and Ireland", *Vitrolife Press Release*, Nov. 2, 2009.

*Primary Examiner* — Travis Hunnings
(74) *Attorney, Agent, or Firm* — Fish & Richardson P.C.

(57) ABSTRACT

A method for coding and identification of biological samples for in vitro fertilization comprises the steps of applying to receptacles intended for unfertilized eggs and sperm, respectively, an identification code characteristic of the patient; placing unfertilized eggs and sperm, respectively, in the receptacles; storing, transporting and admixing the respective samples in receptacles which each carry the same code; and implanting the resulting embryo in the patient. The identification code may based on RFID technology, in which sample vessels (12) are codified by the application of an RFID tag (13).

4 Claims, 1 Drawing Sheet

(56) References Cited

U.S. PATENT DOCUMENTS

| | | |
|---|---|---|
| 7,049,961 B2 | 5/2006 | Maloney |
| 7,072,377 B2 | 7/2006 | Douglas-Hamilton |
| 7,091,864 B2 | 8/2006 | Veitch et al. |
| 7,151,757 B2 | 12/2006 | Beasley et al. |
| 7,187,286 B2 | 3/2007 | Morris et al. |
| 7,194,010 B2 | 3/2007 | Beasley et al. |
| 7,251,489 B2 | 7/2007 | Beasley et al. |
| 7,299,981 B2 | 11/2007 | Hickle et al. |
| 7,359,116 B2 | 4/2008 | Kenny |
| 7,382,258 B2 | 6/2008 | Oldham et al. |
| 7,390,648 B1 | 6/2008 | Palacios-Boyce |
| 7,468,161 B2 | 12/2008 | Reinhardt et al. |
| 7,501,947 B2 | 3/2009 | Youn |
| 7,546,126 B2 | 6/2009 | Beasley et al. |
| 7,564,356 B1 | 7/2009 | Youn |
| 7,663,487 B2 | 2/2010 | Morris et al. |
| 7,699,232 B2 | 4/2010 | Koyama et al. |
| 7,746,229 B2 | 6/2010 | Gräter et al. |
| 7,825,821 B2 | 11/2010 | Luechinger et al. |
| 7,826,938 B2 | 11/2010 | Kato et al. |
| 7,848,905 B2 | 12/2010 | Troxler et al. |
| 7,880,617 B2 | 2/2011 | Morris et al. |
| 7,946,503 B2 | 5/2011 | Koyama et al. |
| 7,958,791 B2 | 6/2011 | Zimmermann et al. |
| 7,962,544 B2 | 6/2011 | Torok et al. |
| 7,991,157 B2 | 8/2011 | Rhoads |
| 8,003,268 B2 | 8/2011 | Smith |
| 8,049,623 B2 | 11/2011 | Morris et al. |
| 8,280,345 B2 | 10/2012 | Twitchell, Jr. |
| 8,301,473 B2 | 10/2012 | Leslie |
| 8,325,637 B2 | 12/2012 | Salsbury et al. |
| 8,360,904 B2 | 1/2013 | Oleson et al. |
| 8,430,326 B2 | 4/2013 | Koyama et al. |
| 8,451,138 B2 * | 5/2013 | Zimmermann .......... A01N 1/02 340/870.31 |
| 8,587,286 B2 | 11/2013 | Inoue et al. |
| 8,599,011 B2 | 12/2013 | Schantz et al. |
| 8,608,535 B2 | 12/2013 | Weston et al. |
| 8,665,071 B2 | 3/2014 | Morris et al. |
| 8,669,848 B2 | 3/2014 | Morris et al. |
| 8,669,849 B2 | 3/2014 | Morris et al. |
| 8,704,634 B2 | 4/2014 | Fantana et al. |
| 8,705,423 B2 | 4/2014 | Salsbury et al. |
| 8,706,325 B2 | 4/2014 | Friedlander et al. |
| 8,881,231 B2 | 11/2014 | Barrus |
| 8,922,587 B2 | 12/2014 | Smyth |
| 8,957,778 B2 | 2/2015 | Adams et al. |
| 8,983,426 B2 | 3/2015 | Cermak et al. |
| 9,019,079 B2 | 4/2015 | Morris et al. |
| 9,039,533 B2 | 5/2015 | Barney et al. |
| 9,058,552 B2 | 6/2015 | Aubert et al. |
| 9,143,843 B2 | 9/2015 | De Luca et al. |
| 9,154,966 B2 | 10/2015 | Bennett et al. |
| 9,211,540 B2 * | 12/2015 | Lansdowne ............ B01L 3/545 |
| 2002/0186968 A1 | 12/2002 | Tanaka |
| 2002/0196146 A1 | 12/2002 | Moore |
| 2006/0057555 A1 * | 3/2006 | Damari .................... A01N 1/02 435/4 |
| 2006/0199196 A1 * | 9/2006 | O'Banion ............... B01L 3/545 435/6.16 |
| 2006/0217185 A1 | 9/2006 | Cavagna |
| 2007/0196909 A1 | 8/2007 | Showalter et al. |
| 2008/0026807 A1 | 1/2008 | Moshal et al. |

* cited by examiner

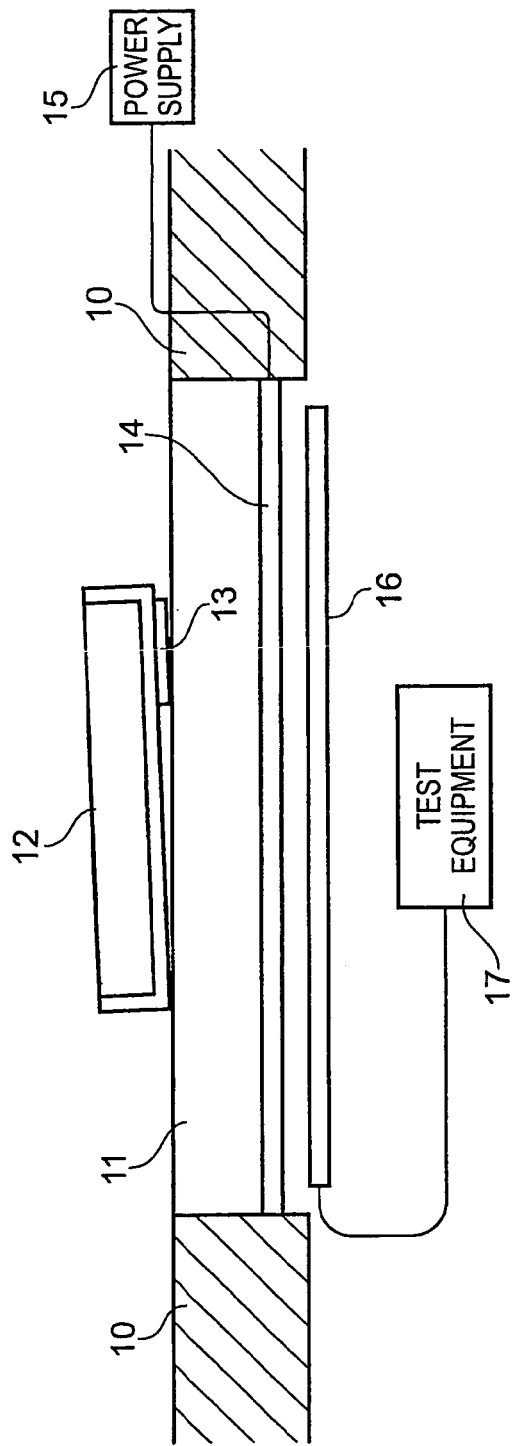
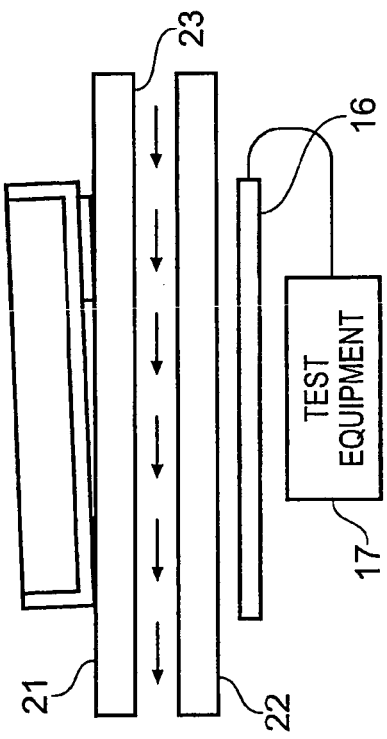

IDENTIFICATION OF BIOLOGICAL SAMPLES

The present application is a divisional of and claims priority from co-pending U.S. patent application Ser. No. 11/597,532, filed 24 Nov. 2006 for "IDENTIFICATION OF BIOLOGICAL SAMPLES".

This invention relates to the identification of biological samples for use in in vitro fertilisation processes.

In vitro fertilisation is a process which is intended to enable a woman, apparently unable to conceive naturally, to gestate and give birth by implantation, in the womb, of an externally-fertilised egg. During the process, unfertilised eggs are collected from the patient's ovaries and admixed with sperm from the woman's partner for fertilisation purposes, the fertilised egg then being re-implanted in the womb for gestation. Clearly, it is important for the procedure to be administered under a rigorous and carefully-controlled protocol to ensure that the eggs are fertilised with sperm from the intended partner; various instances have been reported in the media concerning unintended and highly distressing errors which become apparent following birth. To this end, the Human Fertilisation and Embryology Authority operates a so-called "locked in process", in which the procedure is witnessed at every stage by a person additional to the operative to ensure, as far as possible, that mistakes such as have been made in the past are not repeated in the future. The procedure is consequently expensive to operate and administer and, in any event, the possibility of human error cannot entirely be eliminated.

It is an object of the present invention to provide a procedure and associated apparatus which enables samples to be coded and identified, especially for use in in vitro fertilisation procedures, in a way which falls within the requirements of the regulatory authority, in the UK this being the Human Fertilisation and Embryology Authority.

In one aspect, the invention provides a method for coding and identification of biological samples for in vitro fertilisation, the method comprising the steps of applying to receptacles intended for unfertilised eggs and sperm, respectively, an identification code characteristic of the patient; placing unfertilised eggs and sperm, respectively, in the receptacles; storing, transporting and admixing the respective samples in receptacles which each carry the same code; and implanting the resulting embryo in the patient. Preferably, the identification codes are computer-readable, for example via a bench top reader, and information relating to the vessels and the samples stored therein is maintained in a database which tracks the vessels and samples and can provide information concerning their location at any given time.

Preferably, the identification code is based on RFID technology, in which sample vessels are codified by the application of write-on or printable adhesive labels having an RFID tag permanently attached thereto or incorporated therein, identification being by means of activation by radiation in the form of radio frequency waves, the tag emitting identification signals which can be received by the reader and stored in the database. The RFID tag may alternatively be incorporated in the sample vessel itself. In alternative embodiments, ID tags utilising electromagnetic frequencies other than radio frequencies, such as microwave frequencies, may be used. The database may be controlled by software which includes an anti-collision protocol to discriminate between data received from a plurality of vessels having different identification codes attached thereto.

In another aspect, the invention provides apparatus for identification of biological samples for in vitro fertilisation, the apparatus comprising storage vessels associated with an identification code; and means to read the code and transmit information relating to the samples to a database.

In this specification, the term "vessels" is intended to cover vessels for use at any stage of the overall in vitro fertilisation procedure between initial collection of the egg and sperm samples, storage thereof, admixing thereof for fertilisation purposes and transmission of the embryo to the patient for implantation. Also in this specification, the term "patient" is to be understood, as the context requires, as applying either to the woman or to the male partner.

In operation of the process and as reassurance for the patient, the patient can observe and verify that the initial samples are placed in vessels which correctly identify the patient and that the embryo is also thus identified.

The method of the invention is preferably carried out on a laboratory bench beneath which is located an antenna for transmission of activation radiation and receiving signals emitted by the RFID tag. It is necessary, in order for the samples to remain viable, for the bench surface to be heated to a controlled temperature, preferably in the range 37-42° C. When handling or manipulating samples using conventional techniques, bench surfaces are typically made from stainless steel and heating thereof is by means of pipes disposed under and spaced from the benchtop and through which hot water is circulated, a heat-conductive plate, typically of aluminium or an aluminium alloy, being provided between the pipes and the surface material to equilibrate the temperature differences between the pipes and their surroundings and result in a substantially uniform surface temperature. However, with the method of the present invention, signals between the antenna and samples will not transmit through a metal benchtop, nor will they communicate with an RFID tag in close proximity, typically 1 mm or less, to a metal surface. It is therefore necessary to utilise an electrically non-conducting material for the benchtop, but this militates against the use of temperature control measures which rely on thermal conduction from beneath the surface.

The reading means comprises an antenna and a reader for reading RFID tags. The antenna forms part of an electrical circuit that is configured to optimise the reading of RFID tags on or over the surface. The circuit includes a transformer for providing power to the antenna and also an adjustable capacitor and an adjustable resistor. The transformer is configured to minimise any impedance mismatch between the reader and the antenna to improve the prospect of an RFID tag being readable on or over the entire surface. The adjustable capacitor is set to tune to resonance the coupling between the antenna and the RFID tag over the surface. The adjustable resistor is set to dampen the magnetic field that the antenna produces over the surface so that RFID tags placed over the surface are not "swamped".

According to another aspect, the invention provides a work station providing a warmed surface for supporting biological samples and comprising RFID tag reading means located beneath the surface for reading RFID tags on or over the surface, wherein the station is structured such that warming of the surface is achieved without preventing reading by the reading means of an RFID tag associated with an item placed on the surface.

In one embodiment, the work station comprises a work area defined by an electrically-insulating or resistive plate beneath which in use is located an antenna for transmitting electromagnetic signals to sample receptacles placed on the work area and receiving identification signals therefrom, in which the plate is thermally conducting from one face to the other, the lower surface being in thermal contact with a temperature-controlled heating medium. The work area may be set in a workbench which may be made or example from stainless steel, the work area providing a discrete working zone for the antenna and manipulation operations carried out on the upper surface.

The plate may comprise glass coated on its lower surface with an electrically-conducting heating layer such as indium tin oxide as the heating medium. Alternatively, the plate may comprise upper and lower plate elements defining a cavity between them for containing a liquid heating medium, for example water at a thermostatically-controlled temperature. Preferably, the water is pumped and recirculated through the cavity at a sufficiently high flowrate to minimise the temperature drop across the work area; preferably also, the flow is laminar.

Embodiments of invention will now be described by way of example with reference to the accompanying drawings, of which:

FIG. 1 is a diagrammatic view of a work station utilising one form of heating means; and FIG. 2 is a diagrammatic view of another embodiment using another form of heating means.

With reference firstly to FIG. 1, the apparatus consists essentially of a stainless steel workbench surface (10) having an insert defining a work area and consisting of a toughened glass plate (11). A petri dish (12) having an RFID tag (13) attached to the under surface thereof is placed on the work station. The glass plate (11) carries a lower coating or deposit (14) formed from indium tin oxide, the layer being electrically connected to a power supply to provide an even heating current. An antenna (16) is disposed below the work station and connected to test equipment (17).

In use, the antenna coil transmits activation signals to the RED tag (13) which itself transmits identification signals back to the antenna, the signals being processed in the test equipment (17). The power supply (15) supplies energy to the indium tin oxide layer (14) for heating purposes; the heat generated is transmitted through the plate (11) to maintain the upper surface of the plate at the desired temperature.

With reference to FIG. 2, the work station consists essentially of upper and lower Conan (Registered Trade Mark) plates (21, 22) set into a workbench as shown in FIG. 1. The plates are spaced apart to define a gap (23) through which temperature-controlled water is passed in laminar flow to maintain the upper surface of the work station at the desired temperature. The work station is provided with an antenna and test equipment as described and illustrated with reference to FIG. 1.

The invention claimed is:

1. Apparatus for identification of biological samples for in vitro fertilisation, the apparatus comprising storage vessels associated with an identification code, the identification code being based on RFID technology, sample vessels being codified by the application of an RFID tag;

the apparatus comprising:
a surface defining a work area;
a reader to read the RFID tag;
an antenna for transmission of activation radiation and receiving signals emitted by the RFID tag, the antenna located below the surface;
a resistor to dampen the magnetic field produced by said antenna sufficient to prevent the RFID tag being swamped and still allow communication between the antenna and the RFID tag;
a transformer to provide power to the antenna, the transformer configured to minimise any impedance mismatch between the reader and the antenna; and
an adjustable capacitor to tune to resonance the coupling between the antenna and the RFID tag over the surface of the laboratory bench.

2. The apparatus as claimed in claim 1, wherein the surface is defined by an electrically-insulating or resistive plate, the antenna being located below the plate.

3. The apparatus as claimed in claim 2, wherein the plate comprises glass coated on its lower surface with an electrically-conducting heating layer.

4. The apparatus as claimed in claim 1, wherein the surface is set in a workbench, the work area providing a discrete working zone on the upper surface of the workbench.

* * * * *